(12) United States Patent
Watson et al.

(10) Patent No.: US 12,282,009 B1
(45) Date of Patent: Apr. 22, 2025

(54) SYSTEM FOR MEASURING A GROUND MATERIAL HEALTH LEVEL

(71) Applicant: Open Acre, Issaquah, WA (US)

(72) Inventors: Joshua J. Watson, Seattle, WA (US); Anna K. Assareh, Issaquah, WA (US)

(73) Assignee: Open Acre, Issaquah, WA (US)

( * ) Notice: Subject to any disclaimer, the term of this patent is extended or adjusted under 35 U.S.C. 154(b) by 0 days.

(21) Appl. No.: 18/651,466

(22) Filed: Apr. 30, 2024

(51) Int. Cl.
    *G01N 33/24*     (2006.01)
    *G01N 1/08*     (2006.01)

(52) U.S. Cl.
    CPC ............ *G01N 33/245* (2024.05); *G01N 1/08* (2013.01)

(58) Field of Classification Search
    CPC ................................ G01N 33/245; G01N 1/08
    See application file for complete search history.

(56) References Cited

U.S. PATENT DOCUMENTS

| | | | | |
|---|---|---|---|---|
| 4,732,227 A * | 3/1988 | Wolf | .......................... | E02F 3/06 175/203 |
| 9,127,506 B2 * | 9/2015 | Stimpfle-Ziegler | ..... | E21B 7/005 |
| 9,270,152 B2 * | 2/2016 | Schamberger | .......... | E21B 7/005 |
| 10,309,160 B1 * | 6/2019 | Goren | ...................... | E21B 10/44 |
| 10,689,909 B2 * | 6/2020 | Wang | ....................... | B23B 45/02 |
| 10,914,052 B1 * | 2/2021 | Hemmati | ................ | G02B 6/504 |
| 2023/0392445 A1 * | 12/2023 | Dobernig | ................ | E21B 10/44 |
| 2023/0397516 A1 * | 12/2023 | NewDelman | .......... | A01B 49/06 |
| 2024/0023477 A1 * | 1/2024 | NewDelman | ............ | A01C 5/04 |

FOREIGN PATENT DOCUMENTS

| | | | | |
|---|---|---|---|---|
| CA | 3157940 A1 | * | 5/2021 | ............. B23B 45/02 |
| EP | 1132525 A1 | * | 9/2001 | ............... E02D 5/36 |
| KR | 20190101519 A | * | 9/2019 | |
| KR | 102532933 B1 | * | 5/2023 | |

* cited by examiner

*Primary Examiner* — Octavia Hollington
(74) *Attorney, Agent, or Firm* — Perkins Coie LLP; Alberto Araiza; John Fuller (57) ABSTRACT

The system can comprise an auger including a shank and an auger blade. The auger can include at least one sensor configured to measure multiple characteristics of a ground material beneath the auger. The auger can include a sensor window located on the shank of the auger and a blade scoop located on the auger blade configured to direct the ground material onto the sensor window. The system can further comprise an auger controller configured to control the auger and enable calculation of a health level of the ground material, an accelerometer configured to measure a vibration generated by the auger, a gyroscope configured to determine a drilling angle of the auger, a motor configured to control a speed of the auger, a load sensor configured to measure a force applied to the auger, and a power manager configured to control an amount of energy consumed by the system.

20 Claims, 8 Drawing Sheets

SYSTEM FOR MEASURING A GROUND MATERIAL HEALTH LEVEL

BACKGROUND

Soil, also commonly referred to as earth or dirt, is a mixture of organic matter, minerals, gases, liquids, and organisms that together support the life of plants and soil organisms. Some scientific definitions distinguish dirt from soil by restricting the former term specifically to displaced soil. Soil consists of a solid phase of minerals and organic matter (the soil matrix), as well as a porous phase that holds gases (the soil atmosphere) and water (the soil solution). Accordingly, soil is a three-state system of solids, liquids, and gases. Soil is a product of several factors: the influence of climate, relief (elevation, orientation, and slope of terrain), organisms, and the soil's parent materials (original minerals) interacting over time. It continually undergoes development by way of numerous physical, chemical, and biological processes, which include weathering with associated erosion. Given its complexity and strong internal connectedness, soil ecologists regard soil as an ecosystem.

BRIEF DESCRIPTION OF THE DRAWINGS

Detailed descriptions of implementations of the present invention will be described and explained through the use of the accompanying drawings.

The technologies described herein will become more apparent to those skilled in the art from studying the Detailed Description in conjunction with the drawings. Embodiments or implementations describing aspects of the invention are illustrated by way of example, and the same references can indicate similar elements. While the drawings depict various implementations for the purpose of illustration, those skilled in the art will recognize that alternative implementations can be employed without departing from the principles of the present technologies. Accordingly, while specific implementations are shown in the drawings, the technology is amenable to various modifications.

DETAILED DESCRIPTION

The disclosed technology relates to a system for measuring and calculating the health of a ground material. For instance, ground material can include soil, topsoil, subsoil, dirt, earth, clay, sand, or silt. The system uses an auger to measure the ground material. The auger includes a shank, which can be cylindrical and extend vertically into the ground material when taking a measurement. The auger also can include an auger blade attached to the shank. The auger blade can have a twisted shape that wraps or spirals around the shank. The twisted shape of the auger blade helps break up the ground material, allowing for easier measurement of the ground material. The auger can include at least one sensor configured to measure multiple characteristics of the ground material. Knowing the multiple characteristics of the ground material can indicate the health level of the ground material and what plants can grow and be cultivated in the ground material.

For example, the multiple characteristics measured by the sensor can include a nutrient level, a chemical composition, a moisture level, a temperature, a compaction level, and a potential of hydrogen (pH) level of the ground material. The nutrient level can indicate the number of nutrients found in the ground material. The nutrients measured can include nitrogen, phosphorus, or potassium. A higher nutrient level can indicate that the ground material is more suitable for cultivating crops or plants. The chemical composition can indicate the level and type of inorganic or organic matter found in the ground material, which can be used as an indicator of the health of the ground material. The moisture level can indicate the amount of water in the ground material, which can be used to determine the suitability of cultivating a particular plant. The temperature of the ground material can indicate what plants can grow or germinate in the ground material. The compaction level or density of the ground material can indicate a plant's likelihood of penetrating the ground material and being able to grow. The pH level of the ground material can indicate how the elements in the ground material will affect the plant and the plant's ability to grow or germinate. For example, a ground material with a low pH can cause many elements or nutrients to become less available to the plants while causing elements such as iron, aluminum, or manganese to become toxic to the plants.

In one embodiment, the sensor used to measure the multiple characteristics can be a spectrometer. A spectrometer is any instrument used to measure the variation of a physical characteristic over a given range, i.e., a spectrum. In another embodiment, the sensors used to measure the multiple characteristics can include a range sensor, a moisture sensor, a nutrient sensor, a force sensor, a camera, a temperature sensor, a pH sensor, and/or a chemical sensor. The auger can include a sensor window positioned vertically on the auger shank. The sensor window can be configured to receive the ground material. In one embodiment, the sensor window is constructed from a transparent, durable material such as glass, tempered glass, laminated glass, polycarbonate, acrylic, or any other transparent material. In another embodiment, at least one sensor can be located behind the sensor window. In yet another embodiment, the sensor window can include a non-stick coating configured to prevent the ground material and debris from sticking to or blocking the sensor window. The non-stick coating can be clear and attached to the sensor window. In yet another embodiment, the sensor window can include a brush configured to remove ground material and debris from the sensor window. For example, the brush can be attached to a motor to rotate the brush in order to remove the ground material and debris.

The sensor window can be located on the shank of the auger. In one embodiment, the auger can include a blade scoop configured to direct the ground material onto the sensor window. For example, the blade scoop can be constructed from a section of the auger blade. The blade scoop can be a vertically folded section of the auger blade forming an angle between the auger blade and the blade scoop. The blade scoop can be a perpendicular section of the auger blade and act as a channel for the ground material. The blade scoop can help ensure that a proper amount of ground material is channeled past the sensor window to allow the sensor to make an accurate measurement. For example, inaccurate measurements can cause inaccurate data, leading to lower crop yields, slower-growing plants, and/or plant death.

The system can include an auger controller configured to control the auger. The auger controller includes a motor configured to control the speed of the auger. For instance, the motor can control the rotational speed of the auger by setting the revolutions per minute (rpm) at which the auger rotates. The motor can control the translational speed of the auger. For example, translational speed is the speed at which the auger enters the ground material. The compaction level of the ground material can be calculated by monitoring the load experienced by the motor during the drilling process caused by the auger's interaction with the ground material. Additionally, a load sensor or similar sensor can be added to increase the accuracy of the compaction level calculation. The auger controller can include an accelerometer configured to measure the vibration generated by the auger during the drilling processes. For example, different ground material types or health levels can cause the accelerometer to measure different vibration levels.

The auger controller can include a gyroscope. The gyroscope can be configured to control the drilling angle of the auger. For example, the gyroscope can determine the needed drilling angle for the auger and the current angle of the auger. The gyroscope can adjust the angle of the auger to position the auger to the needed drilling angle. The auger controller can include a power manager configured to control the amount of energy consumed by the system. The auger controller can include a central processing unit (CPU) and a graphics processing unit (GPU). For example, the CPU and the GPU can perform the calculations and processes needed for the motor to determine the compaction level, the accelerometer to determine the vibration level, or the gyroscope to determine the drilling angle. In one embodiment, the auger controller can receive the multiple characteristics measured using the auger and locally calculate the ground material's health level using the CPU and GPU.

The system can include a distance sensor configured to detect the distance or depth from the auger to the ground. For example, the distance sensor can be a range sensor, a camera, a radar sensor, a laser distance sensor, an ultrasonic sensor, and/or any sensor capable of measuring a distance. In one embodiment, the distance sensor is externally mounted to the auger controller. In another embodiment, the distance sensor is mounted to a vehicle. The system can include a vehicle configured to transport the auger and auger controller to the location where a health level will be measured. In one embodiment, the vehicle includes any multi-wheeled powered vehicle capable of transporting the auger and auger controller from one location to another. In another embodiment, the vehicle is an existing piece of equipment, such as a tractor, a car, a truck, an all-terrain vehicle (ATV), or any commercially available vehicle capable of driving off-road. For example, the vehicle can transport the auger and auger controller to a location to measure the health of the ground material. The vehicle includes a mounting structure to couple the auger and auger controller to the vehicle. The vehicle can include a global positioning system (GPS). The GPS can navigate the vehicle to a desired location where a health level can be measured. The vehicle can include a wireless modem configured to connect the system to a Wi-Fi, telecommunications, or wireless network. For example, connecting the vehicle to a wireless network can allow a user to control the vehicle or view the vehicle's location remotely. The wireless modem can also allow the vehicle to remotely receive navigation instructions which autonomously control the movement of the vehicle. The vehicle can include multiple vehicle sensors configured to control the vehicle's location autonomously. The multiple sensors can allow the vehicle to navigate to a desired measurement point autonomously.

To measure the soil health at a location, the system receives the GPS coordinates for a geographic area that contains the ground material to be measured. The system can determine a measurement plan that includes at least one measurement point and the location of the measurement point. The system executes the measurement plan, causing the system to navigate to the location of the measurement point. In one embodiment, the system navigates to the location using the vehicle. When at the measurement location, the system can detect the presence of any debris in the auger's drilling path. For example, debris can include any substance separate from the ground material that could damage the auger, such as rocks, metal, or tree roots. When debris is detected, the system can adjust the location of the measurement point. For example, the measurement point can be adjusted to the closest point from the original measurement point that avoids the debris.

The system can cause the auger to enter the ground material, where the sensor can measure the multiple characteristics of the ground material. The system calculates, using, for example, a machine-learning model (ML) model, the ground material's health level based on the ground material's measured characteristics. In one embodiment, the ML model can be trained using ground material control samples. The ground material control samples can include ground material of different types with varying measurements for the multiple characteristics and, therefore, varying health levels.

In one embodiment, the system can generate a gradient map of the ground material's health level for an area's measurement point. The gradient map can indicate the health level at the measurement point for multiple depths below the ground surface of the ground material. In another embodiment, the system can calculate the health level for multiple measurement points at multiple areas. The system can rank the multiple measurement points based on the health level of the ground material at the measurement point. The system can generate a choropleth map of the multiple areas. A choropleth map uses differences in shading, coloring, or the placing of symbols within predefined areas to indicate the average values of a characteristic, property, or quantity in those areas. The choropleth map generated by the system can indicate which sections or parts of the multiple areas have a suitable health level to cultivate a plant.

In yet another embodiment, the system can log the measurements of the multiple characteristics and the health level of the ground material at each of the multiple measurement points for an area. The system can perform a second measurement of the multiple characteristics and the health level of the ground material at the same measurement points in the area. For example, the second measurement can occur after a predetermined time period has occurred, such as one day, one week, one month, one year, or after a planting season. The system can compare the logged measurements of the multiple characteristics and the health level to the second measurements of the multiple characteristics and the health level of the ground material. The system can generate a ground material report indicating a change in the health level of the ground material for the area over the predetermined time period. For example, the ground material report can include how each of the multiple characteristics of the ground material changed over the predetermined time period.

In one embodiment, the system can determine an action plan for the area based on the health level of the soil. The action plan can include performing more measurements in the area, generating a cultivation plan, or generating a ground material rejuvenation plan. For example, the cultivation plan can include a recommendation of different plant species or crops suitable for the area. For example, the ground material rejuvenation plan includes a list of deficiencies in the ground material and a list of techniques to reduce the deficiencies. For example, deficiencies in the ground material can include a lack of vital nutrients, too much of a particular or multiple nutrients, the presence of a contaminant in the ground material, or an improper ground material compaction level. The system can, therefore, reduce an amount of greenhouse gases by increasing plant growth. Plants remove greenhouse gases such as carbon dioxide from the atmosphere. The system allows for the better cultivation of plants and crops by determining the location and type of plant to be cultivated, thereby increasing plant yield and thus decreasing an amount of greenhouse gases.

The description and associated drawings are illustrative examples and are not to be construed as limiting. This disclosure provides certain details for a thorough understanding and enabling description of these examples. One skilled in the relevant technology will understand, however, that the invention can be practiced without many of these details. Likewise, one skilled in the relevant technology will understand that the invention can include well-known structures or features that are not shown or described in detail to avoid unnecessarily obscuring the descriptions of examples.

Ground Material Health Level Sensing System

Figure 1:
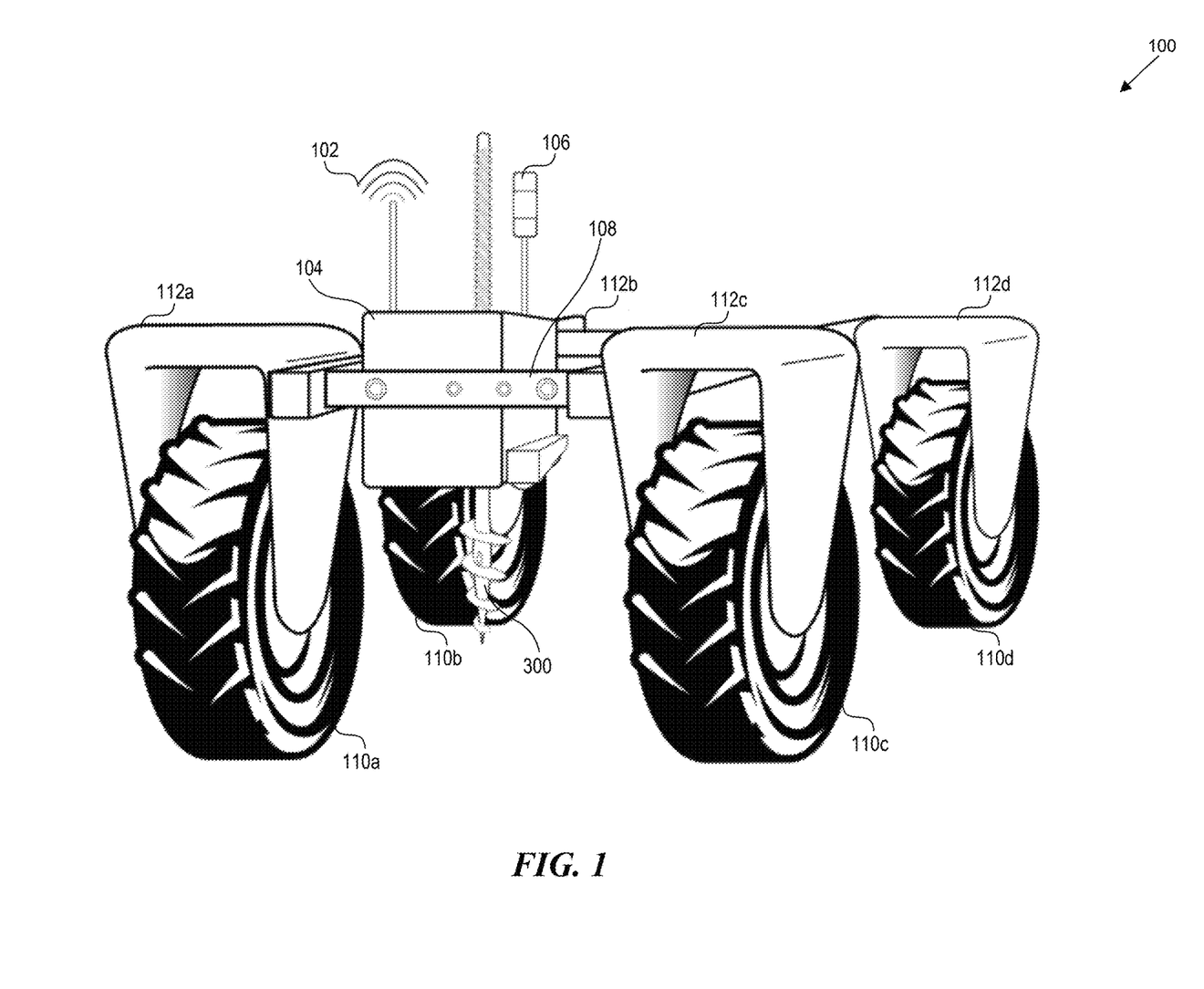
FIG. 1 is an isometric view of a preferred embodiment of the system.

FIG. 1 is an isometric view of a preferred embodiment 100 of the system in which the system is mounted to a vehicle. The system includes auger 300. Auger 300 is mounted below auger controller 104. For example, auger 300 can be attached directly to the underside of auger controller 104. Auger controller 104 can have a cubic-shaped housing that protects the auger controller and a multitude of sensors. Auger 300 and auger controller 104 can be mounted to the vehicle using the mounting hardware 108. Mounting hardware 108 can attach to the outer surface of the auger controller housing. For example, mounting hardware 108 can include screws, bolts, rivets, or any suitable hardware capable of securing auger controller 104 to the vehicle.

The vehicle can include wheel mounts 112a, 112b, 112c, and 112d (wheel mounts 112). Wheel mounts 112 can be configured for large off-road wheels 110a, 110b, 110c, and 110d (wheels 110). An ample clearance allows wheel mounts 112 to receive multiple types of wheels 110 of different sizes, allowing the vehicle to traverse a large variety of terrain. Wheels 110 can be configured to travel off-road without damaging crops and plants. For example, wheels 110 can be configured to position the vehicle body above the top point of the crops to prevent damage to the crops while driving. Additionally, wheels 110 can be spaced appropriately to allow the vehicle to navigate on the same tracks as other farm equipment. For example, a track is a strip of land or ground material where no crops were planted to provide a path for farm equipment.

The vehicle can include a wireless modem 102. Wireless modem 102 can provide cellular or wireless connectivity to the vehicle, allowing the system to be controlled remotely. Wireless modem 102 can be connected to the auger controller and can include GPS capabilities. Wireless modem 102 allows the vehicle to be navigated using a remote control or autonomously without user input. Wireless modem 102 can allow the system to transmit data over a telecommunications network, Wi-Fi network, or other wireless network. The data can include data related to the health level of the ground material. The system can calculate the health level locally or using a remotely located device. The system can additionally transmit the calculated health level and other relevant data, such as the testing location, to a remotely located device using a wireless modem 102. The vehicle can include safety equipment 106. For example, safety equipment 106 can include a light capable of flashing to signal the system's physical location. Additionally, safety equipment 106 can include a sound system that generates auditory notifications such as beeping or a horn to notify nearby personnel about the location of the system or what the system is doing.

Figure 2A:
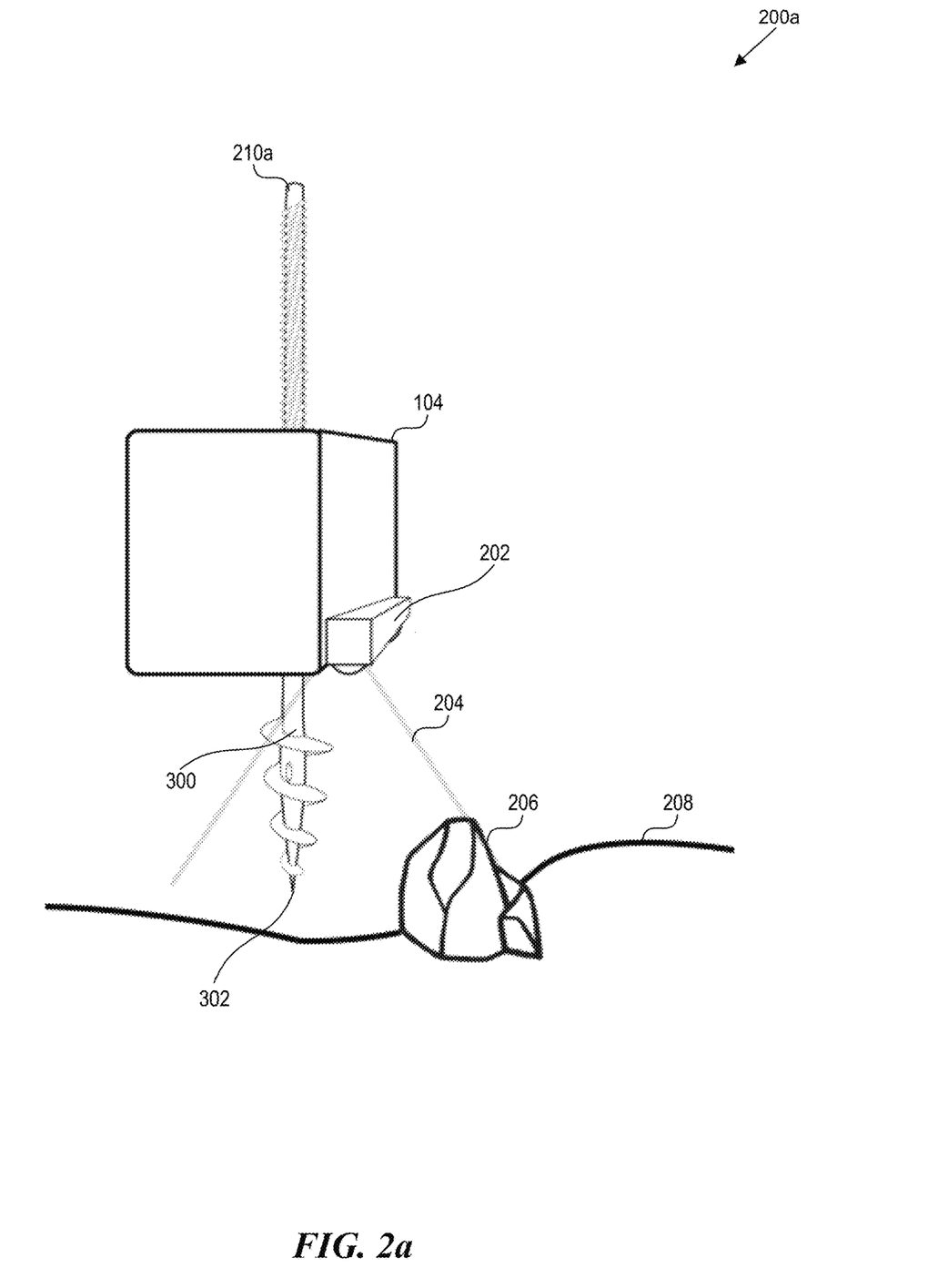
FIG. 2a is an isometric view of an embodiment of the system in a first position.

FIG. 2a is an isometric view of an embodiment 200a of the system in a first position 210a. The first position 210a is before auger 300 is vertically translated toward ground material 208. In the first position 210a, a motor within auger controller 104 can position auger 300 so that the auger tip 302 is positioned away from the ground material 208. For example, auger controller 104 can control the position of auger 300 by rotating a thread through the motor. The system includes a distance sensor 202. Distance sensor 202 is configured to detect a depth or distance from auger tip 302 to ground material 208. Distance sensor 202 can include range sensors, a camera, a radar sensor, a laser distance sensor, an ultrasonic sensor, or any sensor capable of measuring a distance from one point to another. Distance sensor 202 is also configured to detect the presence of any debris 206 that may be present in the path of auger 300. Distance sensor 202 has a detection window 204. Detection window 204 is the area where distance sensor 202 can detect the presence of debris 206.

Figure 2B:
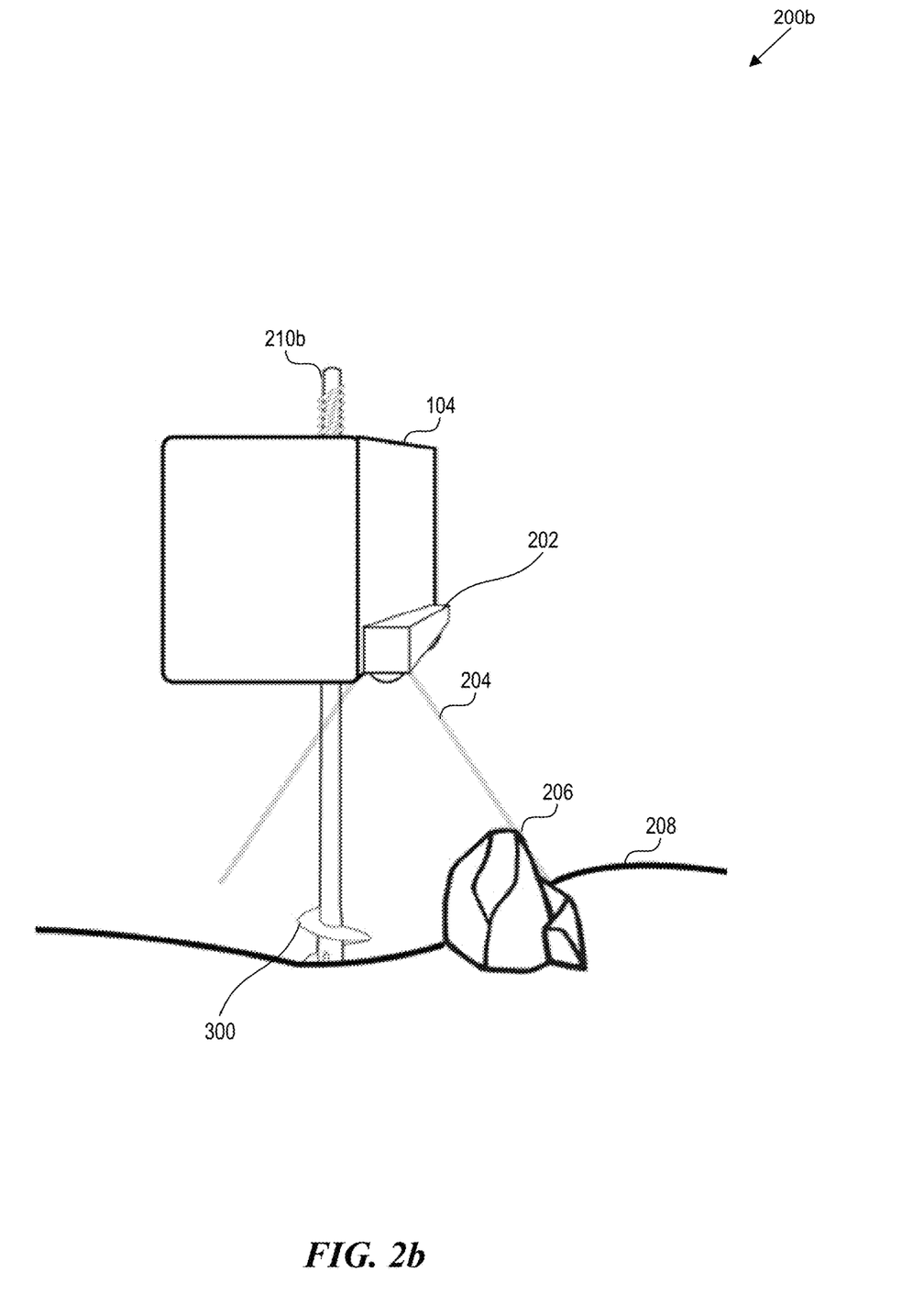
FIG. 2b is an isometric view of an embodiment of the system in a second position.

FIG. 2b is an isometric view of an embodiment 200b of the system in a second position 210b. The second position 210b is after auger 300 has been vertically translated into the ground material 208. In the second position 210b, the motor within auger controller 104 can position auger 300 so that the auger tip 302 is positioned in the ground material 208. The distance sensor 202 can detect debris 206 in the detection window 204. Auger controller 104 can determine that the debris 206 is not in the path of auger 300. The system, therefore, determines that a new testing location is not needed, meaning the system can continue with the testing process. When auger controller 104 determines that debris 206 is in the path of auger 300, the auger controller can notify a user to adjust the testing location or cause the vehicle to move to a different testing location.

Figure 3:
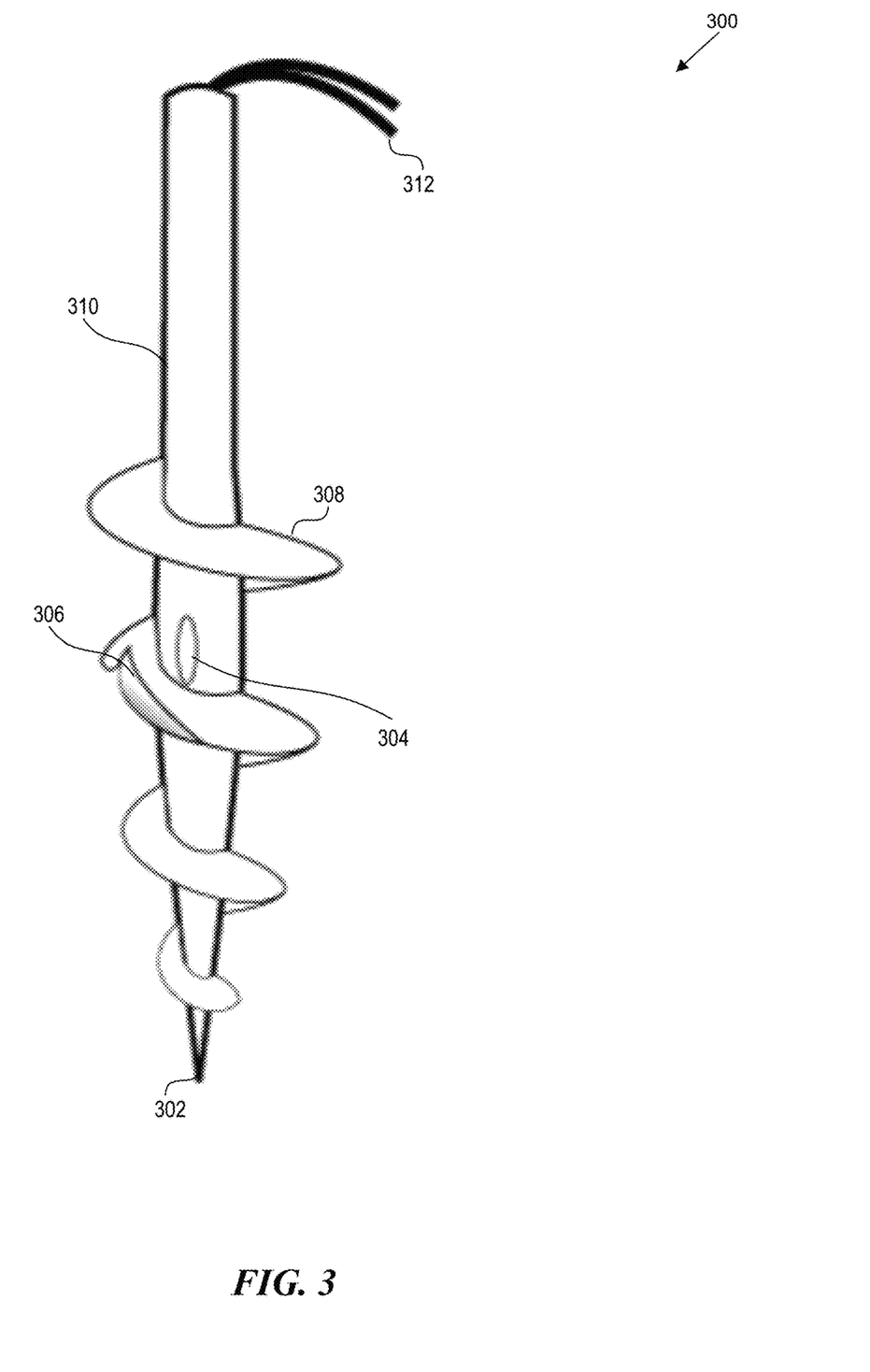
FIG. 3 is a front-facing view of an embodiment of the auger.

FIG. 3 is a front-facing view of an embodiment of auger 300. Auger 300 can include auger tip 302. Auger tip 302 can have a conical shape that comes to a point. The conical shape of auger tip 302 allows auger 300 to pierce the ground material with less resistance when compared to a flat or blunted tip. Auger tip 302 can be attached to or a part of auger shank 310. The auger shank 310 can have a cylindrical shape. In one embodiment, auger shank 310 has a uniform diameter until reaching auger tip 302. In another embodiment, auger shank 310 has a varying diameter. A varying diameter can allow auger 300 to better accommodate sensor 312 or better direct the ground material toward sensor window 304.

Auger blade 308 is attached to auger shank 310. Auger blade 308 can extend helically about the outer diameter of auger shank 310. For example, auger blade 308 can extend a predetermined distance along auger shank 310 starting from auger tip 302. In another example, auger blade 308 can be offset a predetermined distance from auger tip 302 before extending along auger shank 310. Auger blade 308 can extend perpendicularly to or at a predetermined angle from the outer diameter of the auger shank. Auger blade 308 can have a different geometry based on the size of auger 300 or the type of ground material at a location.

The auger blade 308 can include blade scoop 306. Blade scoop 306 can extend from the section of the auger blade in front of sensor window 304. Blade scoop 306 can extend vertically from the auger blade toward the sensor window 304. The geometry of blade scoop 306 can change based on the type of ground material and the size of auger 300 or the sensor window 304. For example, blade scoop 306 can be a separate piece attached to the auger blade 308 or be a bent portion of auger blade 308. Blade scoop 306 can be configured to direct ground material toward sensor window 304. For example, blade scoop 306 can have a flat, concave, or convex geometry to direct different amounts of ground material toward sensor window 304. The geometry of blade scoop 306 can allow the ground material to pass over sensor window 304 without compacting the ground material against sensor window 304. Compacting the ground material can affect the reading of sensor 312, which is located behind sensor window 304, and cause ground material to build up in front of sensor window 304. A buildup of ground material between the sensor window 304 and blade scoop 306 can prevent multiple readings from being taken and can cause the need for manual cleaning of auger 300.

Sensor window 304 can be constructed from a transparent material such as glass or plastic. The size of sensor window 304 can be determined based on the type of sensor 312 housed behind the sensor window 304 or the size of auger 300. Sensor 312 can be connected to auger controller 104 using wires. The wires can be configured to supply sensor 312 with electricity or facilitate the flow of data between the auger controller and sensor 312.

Figure 4:
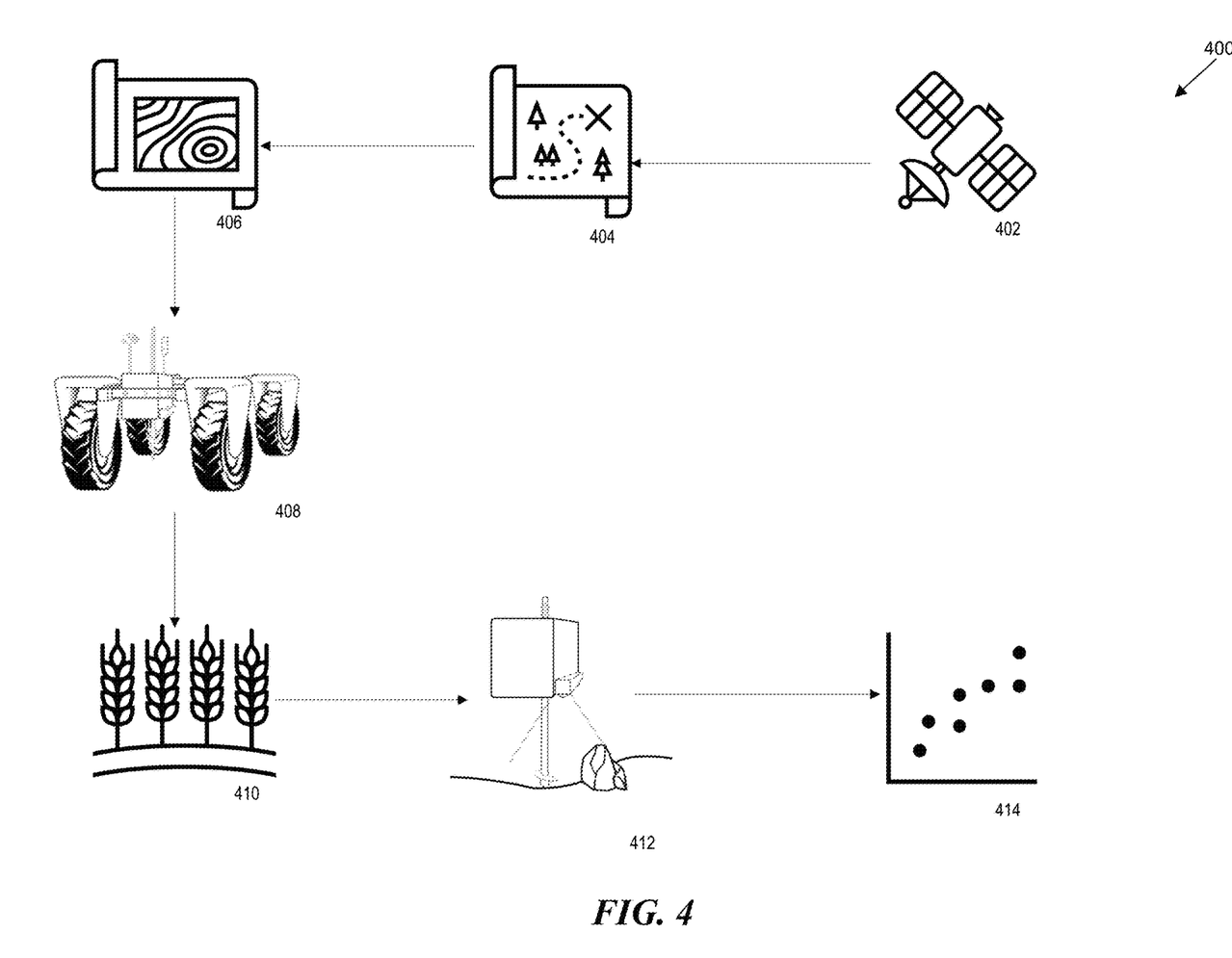
FIG. 4 is a block diagram of an embodiment of the system.

FIG. 4 is a block diagram of an embodiment 400 of the system. The system can receive GPS coordinates from a satellite 402 or another wireless network. The GPS coordinates correspond to the measurement points for a given area. The system can generate a navigation route 404. The navigation route 404 can be a series of driving instructions used to autonomously navigate the system using an off-road vehicle 408 to the measurement area 410. For example, the navigation route can cause vehicle 408 to drive on private property, known paths, public roads, or a combination of the three.

The system generates a measurement plan 406. The measurement plan 406 can include all the measurement points for the measurement area 410. For example, measurement plan 406 can include an expected or known topography of the measurement area 410. Vehicle 408 can, using the navigation route 404, drive to measurement area 410. The measurement area 410 can be cropland with or without crops or any area of land where a health level measurement needs to be taken. The system can begin taking measurements at the measurement area 410. The system can use a detection system 412 to determine if debris in the path of the auger could damage the system and prevent a measurement from being taken. The system can generate graph 414 of the ground material health level. Graph 414 can be a scatterplot, a line graph, a bar chart, or a pie chart. Graph 414 can be generated for a single measurement at one measurement point, multiple measurements at one measurement point, a single measurement at multiple measurement points, or multiple measurements at multiple measurement points.

Figure 5:
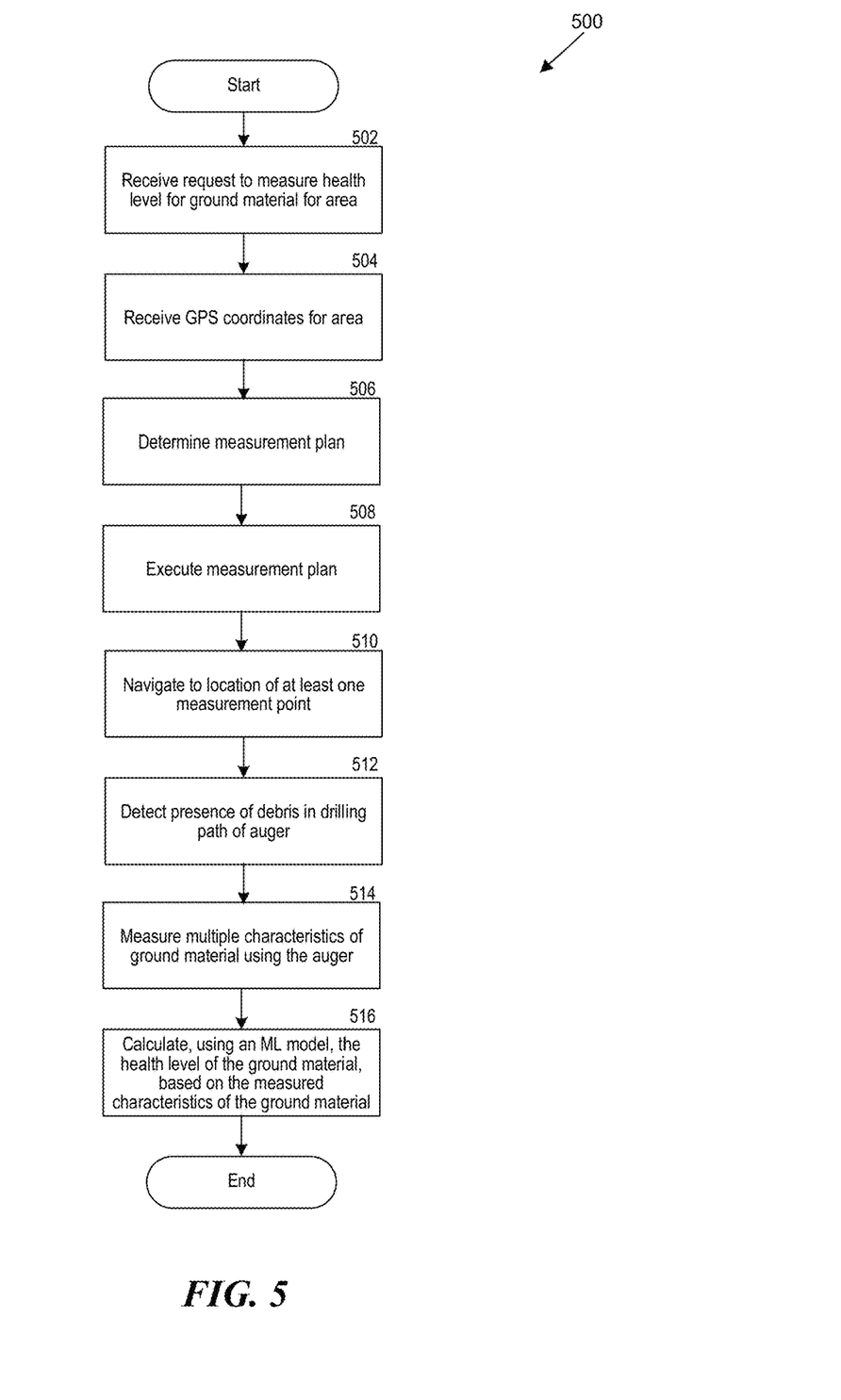
FIG. 5 is a flowchart of an embodiment of the system.

FIG. 5 is a flowchart of an embodiment of the system. In one example, the system can be embodied in a computer system, the system including at least one hardware processor and at least one non-transitory memory storing instructions, which, when executed by the at least one hardware processor, cause the system to perform the process 500.

At step 502, the system can receive a request to measure a health level for ground material for an area. At step 504, the system can receive, from a global positioning system (GPS), coordinates for the area. At step 506, the system can determine a measurement plan. In one example, the measurement plan includes a location of at least one measurement point. At step 508, the system can execute the measurement plan. Executing the measurement plan causes the system to continue to the next step. At step 510, the system can navigate to the location of the at least one measurement point. At step 512, the system can detect for a presence of debris in a drilling path of an auger. The debris is a substance separate from the ground material. Drilling into the debris damages the auger. The system can adjust the location of the at least one measurement point to avoid the debris.

At step 514, the system can measure multiple characteristics of the ground material using the auger. The auger includes at least one sensor configured to measure the multiple characteristics of the ground material. In one example, the multiple characteristics of the ground material include a nutrient level, a chemical composition, a moisture level, a temperature, a compaction level, or a potential of hydrogen (pH) level of the ground material. In one example, the at least one sensor includes a spectrometer, a range sensor, a moisture sensor, a nutrient sensor, a force sensor, a camera, a temperature sensor, a potential of hydrogen (pH) sensor, or a chemical sensor.

At step 516, the system can calculate, using a machine-learning model, the health level of the ground material based on the measured characteristics of the ground material. In one example, the health level is calculated locally on the system. In one example, the system can receive control data for multiple ground material samples. The multiple ground material samples can have varying measurements for the multiple characteristics. The multiple ground material samples can have varying health levels. The system can train the machine-learning model based on the received control data for the multiple ground material samples for each of the multiple measurement points for the area. In another example, the system can generate a gradient map of the health level for the at least one measurement point at the area. The gradient map can indicate the health level of the ground material for multiple depths below a ground surface at the at least one measurement point.

In another example, the system can receive a request to measure a health level for the ground material at multiple areas. The system can determine a measurement plan for the multiple areas. The system can execute the measurement plan for the multiple areas. Executing the measurement plan for the multiple areas can further cause the system to measure the multiple characteristics of the ground material at each of the multiple areas using the auger. The system can calculate the health level of the ground material for each of the multiple areas. The system can rank the multiple areas based on the health level of the area. The system can generate, based on the ranking, a map of the multiple areas. The map can indicate which of the multiple areas is suitable for cultivating a plant.

In another example, the system can determine, based on the health level, an action plan for the ground material for the area. The action plan includes any one of the following: a recommendation to perform more measurements of the ground material at the area, a cultivation plan with recommendations of different plant species suitable to be cultivated at the area, or a ground material rejuvenation plan with a list of deficiencies in the ground material and a list of techniques to reduce the deficiencies in the ground material at the area. In another example, the system indicates the location to cultivate a plant and the type of plant to cultivate, thereby increasing the plant growth and thus reducing an amount of greenhouse gases by increasing the amount of greenhouse gases consumed by the plant.

In another example, the system can log the measurements of the multiple characteristics of the ground material and the health level for the at least one measurement point at the area. The system can perform a second measurement of the multiple characteristics of the ground material after a predetermined time period for the at least one measurement point for the area. The system can calculate a second health level of the ground material for the at least one measurement point at the area. The system can compare the logged measurements of the multiple characteristics and the health level of the ground material to the second measurement of the multiple characteristics and the second health level of the ground material. The system can generate a ground material report indicating a change in the health level of the ground material for the area over the predetermined time period.

Machine-Learning Model

Figure 6:
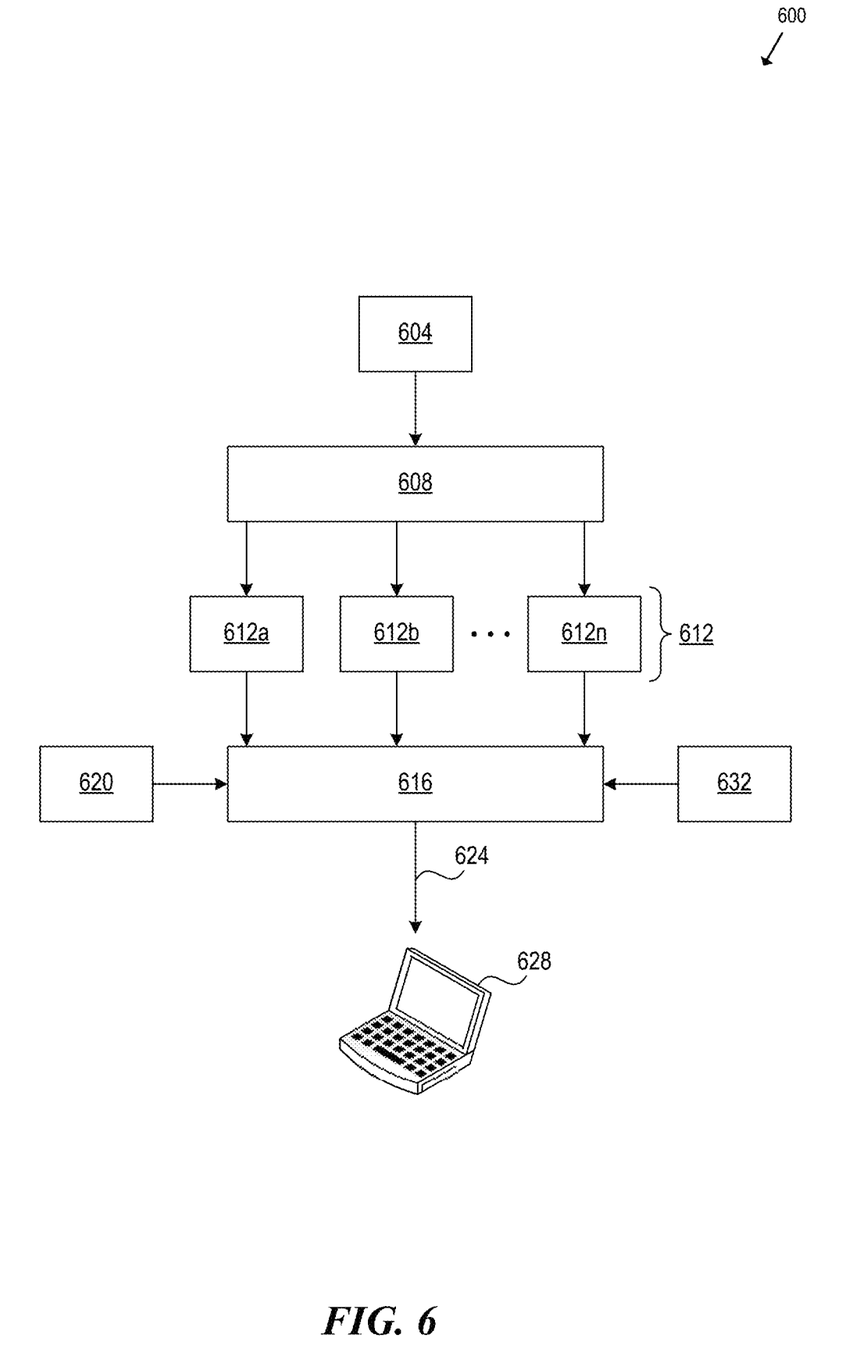
FIG. 6 is a block diagram illustrating an example ML system.

FIG. 6 is a block diagram illustrating an example ML system 600, in accordance with one or more embodiments. Likewise, different embodiments of the ML system 600 include different and/or additional components and are connected in different ways. The ML system 600 is sometimes referred to as an ML module.

The ML system 600 includes a feature extraction module 608 implemented using components of the example computer system 700 illustrated and described in more detail with reference to FIG. 7. In some embodiments, the feature extraction module 608 extracts a feature vector 612 from input data 604. The feature vector 612 includes features 612a, 612b, . . . , 612n. The feature extraction module 608 reduces the redundancy in the input data 604, for example, repetitive data values, to transform the input data 604 into the reduced set of features 612, for example, features 612a, 612b, . . . , 612n. The feature vector 612 contains the relevant information from the input data 604 such that events or data value thresholds of interest are identified by the ML model 616 by using a reduced representation. In some example embodiments, the following dimensionality reduction techniques are used by the feature extraction module 608: independent component analysis, Isomap, kernel principal component analysis (PCA), latent semantic analysis, partial least squares, PCA, multifactor dimensionality reduction, nonlinear dimensionality reduction, multilinear PCA, multilinear subspace learning, semidefinite embedding, autoencoder, and deep feature synthesis.

In alternate embodiments, the ML model 616 performs deep learning (also known as deep structured learning or hierarchical learning) directly on the input data 604 to learn data representations, as opposed to using task-specific algorithms. In deep learning, no explicit feature extraction is performed; the features 612 are implicitly extracted by the ML system 600. For example, the ML model 616 uses a cascade of multiple layers of nonlinear processing units for implicit feature extraction and transformation. Each successive layer uses the output from the previous layer as input. The ML model 616 thus learns in supervised (e.g., classification) and/or unsupervised (e.g., pattern analysis) modes. The ML model 616 learns multiple levels of representations that correspond to different levels of abstraction, wherein the different levels form a hierarchy of concepts. The multiple levels of representation configure the ML model 616 to differentiate features of interest from background features.

In alternative example embodiments, the ML model 616, for example, in the form of a CNN, generates the output 624, without the need for feature extraction, directly from the input data 604. The output 624 is provided to the computer device 628. The computer device 628 is a server, computer, tablet, smartphone, smart speaker, etc., implemented using components of the example computer system 700 illustrated and described in more detail with reference to FIG. 7. In some embodiments, the steps performed by the ML system 600 are stored in memory on the computer device 628 for execution. In other embodiments, the output 624 is displayed on an electronic display of the computer device 628.

A CNN is a type of feed-forward artificial neural network in which the connectivity pattern between its neurons is inspired by the organization of a visual cortex. Individual cortical neurons respond to stimuli in a restricted area of space known as the receptive field. The receptive fields of different neurons partially overlap such that they tile the visual field. The response of an individual neuron to stimuli within its receptive field is approximated mathematically by a convolution operation. CNNs are based on biological processes and are variations of multilayer perceptrons designed to use minimal amounts of preprocessing.

In embodiments, the ML model 616 is a CNN that includes both convolutional layers and max pooling layers. For example, the architecture of the ML model 616 is "fully convolutional," which means that variable-sized sensor data vectors are fed into it. For convolutional layers, the ML model 616 specifies a kernel size, a stride of the convolution, and an amount of zero padding applied to the input of that layer. For the pooling layers, the model 616 specifies the kernel size and stride of the pooling.

In some embodiments, the ML system 600 trains the ML model 616, based on the training data 620, to correlate the feature vector 612 to expected outputs in the training data 620. As part of the training of the ML model 616, the ML system 600 forms a training set of features and training labels by identifying a positive training set of features that have been determined to have a desired property in question and, in some embodiments, forms a negative training set of features that lack the property in question.

The ML system 600 applies ML techniques to train the ML model 616, which, when applied to the feature vector 612, outputs indications of whether the feature vector 612 has an associated desired property or properties, such as a probability that the feature vector 612 has a particular Boolean property, or an estimated value of a scalar property. In embodiments, the ML system 600 further applies dimensionality reduction (e.g., via linear discriminant analysis (LDA), PCA, or the like) to reduce the amount of data in the feature vector 612 to a smaller, more representative set of data.

In embodiments, the ML system 600 uses supervised ML to train the ML model 616, with feature vectors of the positive training set and the negative training set serving as the inputs. In some embodiments, different ML techniques, such as linear support vector machine (linear SVM), boosting for other algorithms (e.g., AdaBoost), logistic regression, naïve Bayes, memory-based learning, random forests, bagged trees, decision trees, boosted trees, boosted stumps, neural networks, CNNs, etc., are used. In some example embodiments, a validation set 632 is formed of additional features other than those in the training data 620, which have already been determined to have or to lack the property in question. The ML system 600 applies the trained ML model 616 to the features of the validation set 632 to quantify the accuracy of the ML model 616. Common metrics applied in accuracy measurement include Precision and Recall, where Precision refers to a number of results the ML model 616 correctly predicted out of the total it predicted and Recall is a number of results the ML model 616 correctly predicted out of the total number of features that had the desired property in question. In some embodiments, the ML system 600 iteratively retrains the ML model 616 until the occurrence of a stopping condition, such as the accuracy measurement indication that the ML model 616 is sufficiently accurate, or a number of training rounds have taken place. In embodiments, the validation set 632 includes data corresponding to confirmed locations, dates, times, activities, or combinations thereof. This allows the detected values to be validated using the validation set 632. The validation set 632 is generated based on the analysis to be performed.

Computer System

Figure 7:
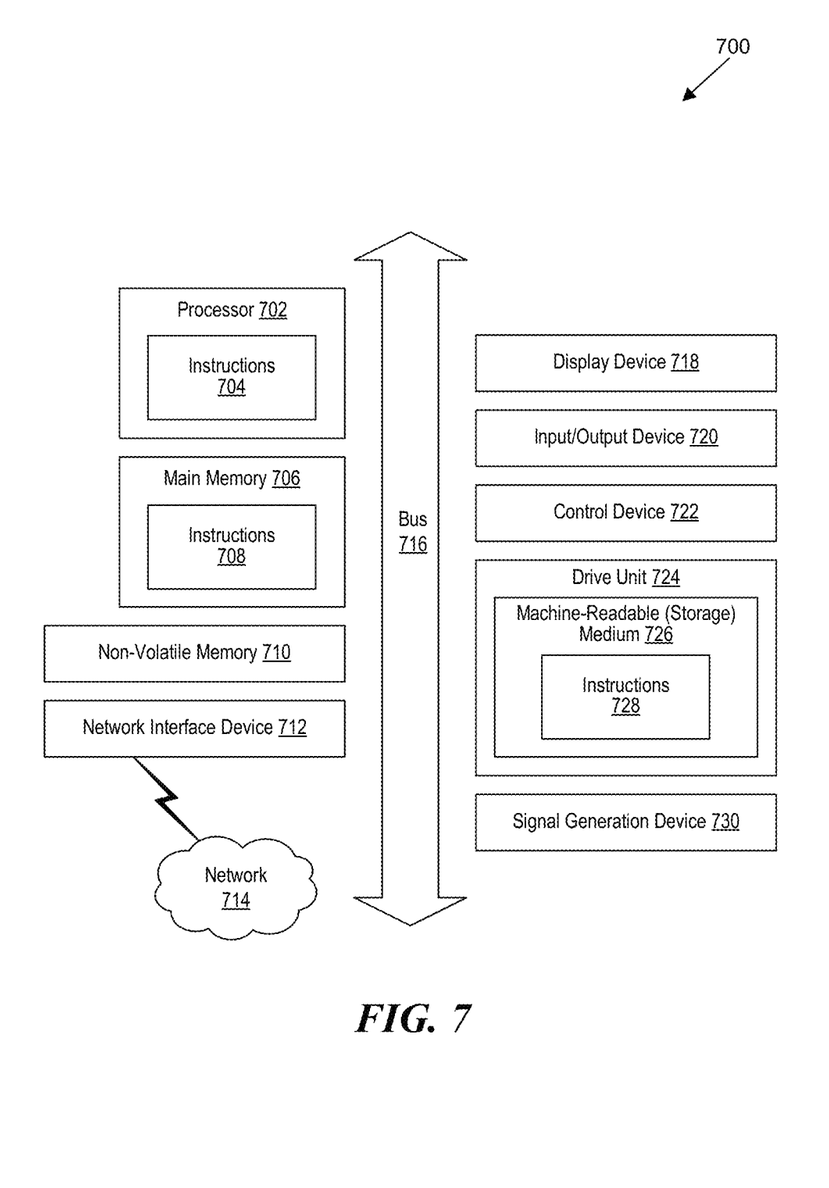
FIG. 7 is a block diagram that illustrates an example of a computer system in which at least some operations described herein can be implemented.

FIG. 7 is a block diagram that illustrates an example of a computer system 700 in which at least some operations described herein can be implemented. As shown, the computer system 700 can include: one or more processors 702, main memory 706, non-volatile memory 710, a network interface device 712, a video display device 718, an input/output device 720, a control device 722 (e.g., keyboard and pointing device), a drive unit 724 that includes a machine-readable (storage) medium 726, and a signal generation device 730 that are communicatively connected to a bus 716. The bus 716 represents one or more physical buses and/or point-to-point connections that are connected by appropriate bridges, adapters, or controllers. Various common components (e.g., cache memory) are omitted from FIG. 7 for brevity. Instead, the computer system 700 is intended to illustrate a hardware device on which components illustrated or described relative to the examples of the figures and any other components described in this specification can be implemented.

The computer system 700 can take any suitable physical form. For example, the computing system 700 can share a similar architecture as that of a server computer, personal computer (PC), tablet computer, mobile telephone, game console, music player, wearable electronic device, network-connected ("smart") device (e.g., a television or home assistant device), AR/VR systems (e.g., head-mounted display), or any electronic device capable of executing a set of instructions that specify action(s) to be taken by the computing system 700. In some implementations, the computer system 700 can be an embedded computer system, a system-on-chip (SOC), a single-board computer system (SBC), or a distributed system such as a mesh of computer systems, or it can include one or more cloud components in one or more networks. Where appropriate, one or more computer systems 700 can perform operations in real time, in near real time, or in batch mode.

The network interface device 712 enables the computing system 700 to mediate data in a network 714 with an entity that is external to the computing system 700 through any communication protocol supported by the computing system 700 and the external entity. Examples of the network interface device 712 include a network adapter card, a wireless network interface card, a router, an access point, a wireless router, a switch, a multilayer switch, a protocol converter, a gateway, a bridge, a bridge router, a hub, a digital media receiver, and/or a repeater, as well as all wireless elements noted herein.

The memory (e.g., main memory 706, non-volatile memory 710, machine-readable medium 726) can be local, remote, or distributed. Although shown as a single medium, the machine-readable medium 726 can include multiple media (e.g., a centralized/distributed database and/or associated caches and servers) that store one or more sets of instructions 728. The machine-readable medium 726 can include any medium that is capable of storing, encoding, or carrying a set of instructions for execution by the computing system 700. The machine-readable medium 726 can be non-transitory or comprise a non-transitory device. In this context, a non-transitory storage medium can include a device that is tangible, meaning that the device has a concrete physical form, although the device can change its physical state. Thus, for example, non-transitory refers to a device remaining tangible despite this change in state.

Although implementations have been described in the context of fully functioning computing devices, the various examples are capable of being distributed as a program product in a variety of forms. Examples of machine-readable storage media, machine-readable media, or computer-readable media include recordable-type media such as volatile and non-volatile memory 710, removable flash memory, hard disk drives, optical disks, and transmission-type media such as digital and analog communication links.

In general, the routines executed to implement examples herein can be implemented as part of an operating system or a specific application, component, program, object, module, or sequence of instructions (collectively referred to as "computer programs"). The computer programs typically comprise one or more instructions (e.g., instructions 704, 708, 728) set at various times in various memory and storage devices in computing device(s). When read and executed by the processor 702, the instruction(s) cause the computing system 700 to perform operations to execute elements involving the various aspects of the disclosure.

Remarks

The terms "example," "embodiment," and "implementation" are used interchangeably. For example, references to "one example" or "an example" in the disclosure can be, but not necessarily are, references to the same implementation; and such references mean at least one of the implementations. The appearances of the phrase "in one example" are not necessarily all referring to the same example, nor are separate or alternative examples mutually exclusive of other examples. A feature, structure, or characteristic described in connection with an example can be included in another example of the disclosure. Moreover, various features are described that can be exhibited by some examples and not by others. Similarly, various requirements are described that can be requirements for some examples but not for other examples.

The terminology used herein should be interpreted in its broadest reasonable manner, even though it is being used in conjunction with certain specific examples of the invention. The terms used in the disclosure generally have their ordinary meanings in the relevant technical art, within the context of the disclosure, and in the specific context where each term is used. A recital of alternative language or synonyms does not exclude the use of other synonyms. Special significance should not be placed upon whether or not a term is elaborated or discussed herein. The use of highlighting has no influence on the scope and meaning of a term. Further, it will be appreciated that the same thing can be said in more than one way.

Unless the context clearly requires otherwise, throughout the description and the claims, the words "comprise," "comprising," and the like are to be construed in an inclusive sense, as opposed to an exclusive or exhaustive sense—that is to say, in the sense of "including, but not limited to." As used herein, the terms "connected," "coupled," and any variants thereof mean any connection or coupling, either direct or indirect, between two or more elements; the coupling or connection between the elements can be physical, logical, or a combination thereof. Additionally, the words "herein," "above," "below," and words of similar import can refer to this application as a whole and not to any particular portions of this application. Where context permits, words in the above Detailed Description using the singular or plural number may also include the plural or singular number, respectively. The word "or" in reference to a list of two or more items covers all of the following interpretations of the word: any of the items in the list, all of the items in the list, and any combination of the items in the list. The term "module" refers broadly to software components, firmware components, and/or hardware components.

While specific examples of technology are described above for illustrative purposes, various equivalent modifications are possible within the scope of the invention, as those skilled in the relevant art will recognize. For example, while processes or blocks are presented in a given order, alternative implementations can perform routines having steps, or employ systems having blocks, in a different order, and some processes or blocks may be deleted, moved, added, subdivided, combined, and/or modified to provide alternative or sub-combinations. Each of these processes or blocks can be implemented in a variety of different ways. Also, while processes or blocks are at times shown as being performed in series, these processes or blocks can instead be performed or implemented in parallel, or can be performed at different times. Further, any specific numbers noted herein are only examples such that alternative implementations can employ differing values or ranges.

Details of the disclosed implementations can vary considerably in specific implementations while still being encompassed by the disclosed teachings. As noted above, particular terminology used when describing features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific examples disclosed herein, unless the above Detailed Description explicitly defines such terms. Accordingly, the actual scope of the invention encompasses not only the disclosed examples but also all equivalent ways of practicing or implementing the invention under the claims. Some alternative implementations can include additional elements to those implementations described above or include fewer elements.

Any patents and applications and other references noted above, and any that may be listed in accompanying filing papers, are incorporated herein by reference in their entireties, except for any subject matter disclaimers or disavowals, and except to the extent that the incorporated material is inconsistent with the express disclosure herein, in which case the language in this disclosure controls. Aspects of the invention can be modified to employ the systems, functions, and concepts of the various references described above to provide yet further implementations of the invention.

To reduce the number of claims, certain implementations are presented below in certain claim forms, but the applicant contemplates various aspects of an invention in other forms. For example, aspects of a claim can be recited in a means-plus-function form or in other forms, such as being embodied in a computer-readable medium. A claim intended to be interpreted as a means-plus-function claim will use the words "means for." However, the use of the term "for" in any other context is not intended to invoke a similar interpretation. The applicant reserves the right to pursue such additional claim forms either in this application or in a continuing application.

We claim:

1. A system comprising:
   an auger including a shank and an auger blade, the auger including:
      at least one sensor configured to measure multiple characteristics of a ground material beneath the auger,
         wherein the multiple characteristics of the ground material include a nutrient level, a chemical composition, a moisture level, a temperature, a compaction level, or a potential of hydrogen (pH) level of the ground material;
      a sensor window located directly on the shank of the auger configured to receive the ground material,
         wherein the at least one sensor is positioned within the shank and behind the sensor window; and
      a blade scoop located on the auger blade configured to direct the ground material onto the sensor window; and
   an auger controller communicatively coupled to the auger, and configured to control the auger and enable calculation of a health level of the ground material;
   an accelerometer configured to measure a vibration generated by the auger drilling into the ground material;
   a gyroscope configured to determine a drilling angle of the auger,
      wherein the gyroscope can adjust the drilling angle for the auger based on the determined drilling angle;
   a motor configured to control a speed of the auger,
      wherein the speed of the auger includes a rotational drilling speed and a translational drilling speed, and
      wherein the compaction level is calculated based on a load experienced by the motor when the auger interacts with the ground material;
   a power manager configured to control an amount of energy consumed by the system.

2. The system of claim 1 further comprising:
   a distance sensor configured to detect a depth from a drilling tip of the auger to a ground surface,
      wherein the distance sensor includes a range sensor, a camera, a radar sensor, a laser distance sensor, or an ultrasonic sensor, and
      wherein the distance sensor is externally mounted to the auger controller; and
   a load sensor configured to measure a force applied to the auger,
      wherein the force is caused by an interaction between the auger and the ground material, and
      wherein the force measurement is used to improve the accuracy of the compaction level calculation.

3. The system of claim 1, wherein the auger further comprises:
a transparent non-stick coating on the sensor window configured to prevent the ground material and debris from attaching to or blocking the sensor window.

4. The system of claim 1 further comprising:
a vehicle configured to transport the auger and auger controller to a location to measure the health level of the ground material comprising:
   a mounting structure configured to secure the auger controller and the auger to the vehicle;
   a global positioning system;
   a wireless modem configured to connect to a Wi-Fi or telecommunications network; and
   multiple vehicle sensors configured to autonomously control a movement of the vehicle.

5. The system of claim 1, wherein the at least one sensor includes:
a spectrometer,
a range sensor,
a moisture sensor,
a nutrient sensor,
a force sensor,
a camera,
a temperature sensor,
a potential of hydrogen (pH) sensor, or
a chemical sensor.

6. The system of claim 1, wherein the auger controller further comprises:
a machine-learning model configured to locally calculate the health level of the ground material at the auger controller based on the measured multiple characteristics of the ground material.

7. The system of claim 6, wherein the locally calculated health level of the ground material is transmitted to a remotely located model to generate recommendations for the ground material.

8. A system comprising:
an auger including a shank and an auger blade, the auger including:
   at least one sensor configured to measure multiple characteristics of a ground material beneath the auger,
      wherein the multiple characteristics of the ground material include a nutrient level, a chemical composition, a moisture level, a temperature, a compaction level, or a potential of hydrogen (pH) level of the ground material;
   a sensor window located directly on the shank of the auger configured to receive the ground material,
      wherein the at least one sensor is positioned within the shank and behind the sensor window; and
an auger controller communicatively coupled to the auger, and configured to control the auger and enable calculation of a health level of the ground material.

9. The system of claim 8 further comprising:
a distance sensor configured to detect a depth from a drilling tip of the auger to a ground surface,
   wherein the distance sensor includes a range sensor, a camera, a radar sensor, a laser distance sensor, or an ultrasonic sensor, and
   wherein the distance sensor is externally mounted to the auger controller; and
a load sensor configured to measure a force applied to the auger,
   wherein the force is caused by an interaction between the auger and the ground material.

10. The system of claim 8 further comprising:
a vehicle configured to transport the auger and auger controller to a location to measure the health level of the ground material comprising:
   a mounting structure configured to secure the auger controller and the auger to the vehicle;
   a global positioning system;
   a wireless modem configured to connect to a Wi-Fi or telecommunications network; and
   multiple vehicle sensors configured to autonomously control a movement of the vehicle.

11. The system of claim 8, wherein the at least one sensor includes:
a spectrometer,
a range sensor,
a moisture sensor,
a nutrient sensor,
a force sensor,
a camera,
a temperature sensor,
a potential of hydrogen (pH) sensor, or
a chemical sensor.

12. The system of claim 8, wherein the auger controller further comprises:
a machine-learning model configured to locally calculate the health level of the ground material at the auger controller based on the measured multiple characteristics of the ground material.

13. An auger system comprising:
a shank;
an auger blade;
at least one sensor configured to measure multiple characteristics of a ground material beneath the auger,
   wherein the multiple characteristics of the ground material include a nutrient level, a chemical composition, a moisture level, a temperature, a compaction level, or a potential of hydrogen (pH) level of the ground material;
a sensor window located directly on the shank of the auger configured to receive the ground material,
   wherein the at least one sensor is positioned within the shank and behind the sensor window; and
an auger controller communicatively coupled to the auger, and configured to control the auger and enable calculation of a health level of the ground material.

14. The auger system of claim 13, further comprising:
a transparent non-stick coating on the sensor window configured to prevent the ground material and debris from attaching to or blocking the sensor window.

15. The auger system of claim 13, wherein the at least one sensor includes:
a spectrometer,
a range sensor,
a moisture sensor,
a nutrient sensor,
a force sensor,
a camera,
a temperature sensor,
a potential of hydrogen (pH) sensor, or
a chemical sensor.

16. The auger system of claim 13, further comprising:
an accelerometer configured to measure a vibration generated by the auger drilling into the ground material.

17. The auger system of claim 13, further comprising:
a gyroscope configured to determine a drilling angle of the auger, wherein the gyroscope can adjust the drilling angle for the auger based on the determined drilling angle.

18. The auger system of claim 13, further comprising:
a vehicle configured to transport the auger and auger controller to a location to measure the health level of the ground material.

19. The auger system of claim 18, wherein the vehicle further includes:
multiple vehicle sensors configured to autonomously control a movement of the vehicle.

20. The auger system of claim 13, wherein the auger controller further comprises:
a machine-learning model configured to locally calculate the health level of the ground material at the auger controller based on the measured multiple characteristics of the ground material,
wherein the locally calculated health level of the ground material is transmitted to a remotely located model to generate recommendations for the ground material.

* * * * *